United States Patent [19]

Samuels

[11] Patent Number: 5,695,332
[45] Date of Patent: Dec. 9, 1997

[54] ORTHODONTIC FACEBOW WITH LOCKING CATCH

[76] Inventor: Russell H. A. Samuels, Deane Cottage, 23 Main Street, Cadeby, Warwickshire, CV13 0AX, United Kingdom

[21] Appl. No.: 604,155

[22] Filed: Feb. 20, 1996

[30] Foreign Application Priority Data

Nov. 23, 1995 [GB] United Kingdom ............... 9528935

[51] Int. Cl.[6] .................................................. A61C 7/00
[52] U.S. Cl. ............................................................ 433/5
[58] Field of Search ............................. 433/5, 17, 22, 433/18, 19

[56] References Cited

U.S. PATENT DOCUMENTS

| | | | |
|---|---|---|---|
| 3,036,380 | 5/1962 | Martinek et al. | 433/5 |
| 4,040,188 | 8/1977 | Masel . | |
| 4,087,915 | 5/1978 | Andrews . | |
| 4,212,637 | 7/1980 | Dougherty et al. | 433/5 |
| 4,245,984 | 1/1981 | Hamill, Jr. | 433/5 |
| 4,419,077 | 12/1983 | Asher | 433/5 |
| 4,588,380 | 5/1986 | Toll | 433/5 |
| 4,764,110 | 8/1988 | Dougherty | 433/5 |

FOREIGN PATENT DOCUMENTS

| | | | |
|---|---|---|---|
| 2708723 | 9/1978 | Germany | 433/5 |

*Primary Examiner*—Cary E. O'Connor
*Attorney, Agent, or Firm*—Jack C. Munro

[57] ABSTRACT

A facebow 10 which has a locking catch 40 mounted to each of the arms 16 and 17 of an inner bow 11. The end portion 13 of each arm 16 and 17 is inserted through a tube 22 of an orthodontic appliance, such as a bracket 15 which is fixed to a respective tooth T. The locking catch 40 includes a hook 42 for engaging the end portion 13 of the arm 16 or 17 which projects distally (rearwardly) of the tube 22. The locking catch 40 is easy for the user to engage and disengage, but when engaged, effectively locks the arms 16 and 17 of the inner bows 11 preventing accidental withdrawal from the respective tubes 22.

8 Claims, 2 Drawing Sheets

ORTHODONTIC FACEBOW WITH LOCKING CATCH

BACKGROUND OF THE INVENTION

1) Field of the Invention

This invention relates to a facebow for use in orthodontics, and more specifically relates to a locking catch for such a facebow.

2) Description of the Prior Art

Facebows are used in orthodontics to move pairs of molar teeth distally (rearwardly) in a patient's mouth, or to anchor such against movement. A metal band is cemented around each of the teeth to be moved or anchored, the band having a buccally (outwardly) projecting bracket affixed to it. The bracket has a tube positioned along a line parallel to the buccal surface of the molar teeth. The facebow comprises an inner, C-shaped, metal bow having opposite ends or feet which engage within the tubes of the aforementioned brackets. In use, the inner bow extends around the outer labial and buccal portions of the patient's teeth inside the mouth. The facebow also comprises an outer bow which is joined at its middle to the middle of the inner bow. The outer bow has arms which extend posteriorly (rearwardly) around the outside of the patient's cheeks. The free ends of the arms of the outer bow are provided with hooks. An elasticated or spring-loaded strap is attached to the hooks on the outer bow and connected around the back of the head and/or neck of the human user. Thus the facebow is pulled posteriorly by the strap and, because the facebow is fixed to the patient's teeth, a distal (rearward) force is applied to the teeth. Over a period of time the teeth are moved distally, or alternatively are held against forward movement.

The facebow is held to the teeth merely by way of the ends of the inner bow engaging within the tubes of the brackets. The tension developed by the head and/or neck strap keeps the inner bow in engagement with the brackets on both teeth. However, should the strap break or become detached from the facebow for whatever reason, then the inner bow is free to disengage from the brackets. The ends of the inner bow are relatively sharp, and could possibly penetrate the user's cheek or even an eye while he or she is asleep.

Facebows have been proposed which include a locking catch on each arm of the inner bow: an end portion of the locking catch snap-engages behind a projection on the bracket which is fixed to the tooth. The locking catch is effective in preventing accidental removal of the facebow. However, the locking catch must be designed to match the particular shape, size and construction of the bracket, which vary from one manufacturer to another. Also in these previously proposed facebows, the locking catch comprises a length of wire which is soldered or welded to the arm of the inner bow, then extends forwardly from its point of attachment, loops to form a biasing spring, and then extends rearwardly to terminate as a snap-engaging catch. The locking catch is relatively short in length and therefore relatively inaccessible for the user to engage and displace for disengaging the catch to remove the facebow from the mouth.

SUMMARY OF THE INVENTION

In accordance with this invention, there is provided a facebow which comprises an outer bow having opposite ends for attachment to a head and/or neck strap, an inner bow connected to said outer bow, the inner bow comprising two arms having free ends for insertion through tubular formations of an orthodontic appliance, said tubular formations being, in use, secured adjacent opposed teeth which are to be moved distally or restrained against forward movement, and a locking catch mounted to each arm of the inner bow and extending distally to terminate in a hook arranged to engage an end portion of that arm which projects distally from the tubular formation of the respective bracket. Preferably each locking catch extends distally (rearwardly) from its point of mounting to the respective arm of the inner bow, and generally parallel to that arm. Preferably each locking catch is formed with a spring biasing portion adjacent its point of mounting to the respective arm of the inner bow. Preferably the locking catch is formed of a length of spring wire. Preferably this length of wire is mounted by soldering or welding to the respective arm of the inner bow. Preferably each arm of the inner bow is formed with a loop adjacent its free inner end. By using a pair of pliers or a similar tool, the orthodontist can tighten or widen this loop to adjust the effective length of the respective arm of the inner bow, or he or she can bend the arm at the location of this loop so as to adjust the orientation of the free inner end of the arm to align accurately with the tubular formation of the bracket fixed to the tooth. Preferably each locking catch is also formed with a loop enabling the orthodontist to adjust the effective length of the catch to correspond with adjustments made to the length of the respective arm of the inner bow.

It will be appreciated that because each locking catch engages with the arm itself of the inner bow, the facebow is relatively independent of the precise size and construction of the orthodontic appliance with which it is used. The same type of facebow can therefore be used with the appliances of various different manufacturers, and can particularly be used with appliances having tubular formations of different lengths.

Also in accordance with this invention, there is provided a locking catch for a facebow, the locking catch comprising an elongated member having one end for mounting to a respective arm of the inner bow of the facebow, and an opposite end which terminates in a hook arranged to engage an end portion of the arm of the inner bow of the facebow.

DETAILED DESCRIPTION OF THE PREFERRED EMBODIMENT

Figure 1:
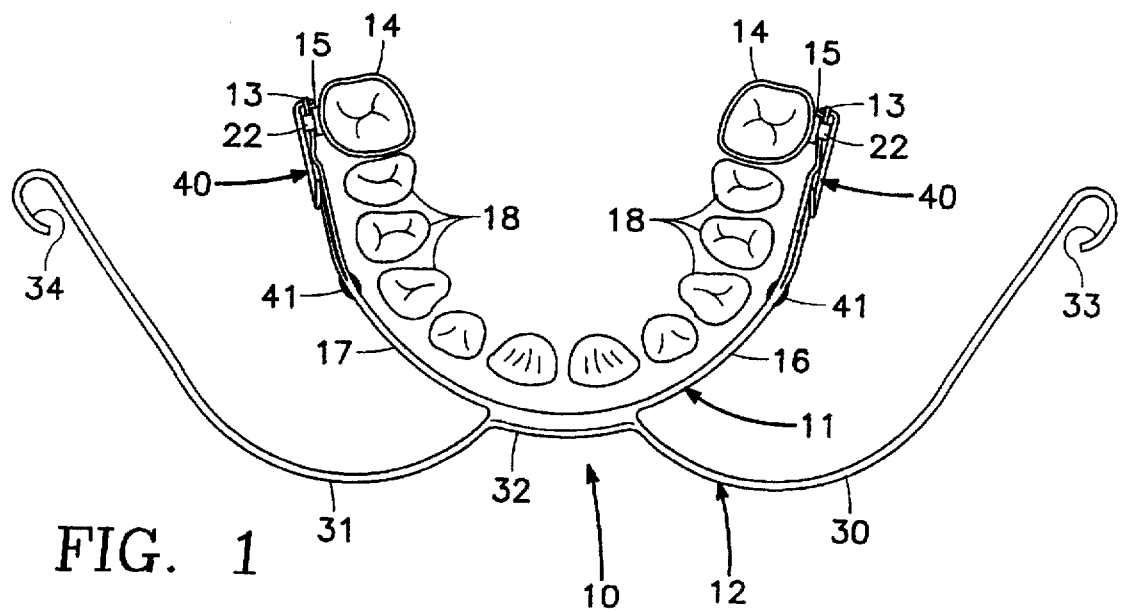
FIG. 1 is an occlusal (bottom) view of an embodiment of facebow of this invention when fitted to a set of top teeth.

Referring to FIG. 1 of the drawings, there is shown a wire facebow 10 comprising a generally C-shaped inner bow 11 connected at the middle thereof to the middle portion 32 of an outer bow 12 which has two arms 30 and 31 extending outwardly and rearwardly. Inner bow 11 has a similar pair of arms 16 and 17 with arm 16 being in juxtaposition with arm 30 and arm 17 being in juxtaposition with arm 31. Opposite ends of the outer bow 12 are formed into forward-facing hooks 33 and 34 for attachment to a head and/or neck strap (not shown).

In accordance with usual practices, a metal band 14 is cemented in position around each of the teeth T which are to be moved distally (rearwardly) or alternatively to be restrained against forward movement. Each metal band 14 has a bracket 15 fixed to it as by welding. The metal band 14 includes a tube 22 which has a longitudinal through opening (not shown) the longitudinal center axis of which is directed forwardly along the buccal surface of the teeth 18. Straight end portions 13 of each of the arms 16 and 17 of the inner bow 11 are, when in use, inserted through the through opening of each tube 22. It is to be understood that only one end portion 13 connects with a tube 22.

An occlusally (downward) projecting, U-shaped loop 24 is formed adjacent the straight end portion 13 of each arm 16 and 17 of the inner bow 11, to enable the orthodontist to adjust the direction of each straight end portion 13 to align with the through opening of its corresponding tube 22. The loop 24 can be occlusally (downwardly) or gingivally (upwardly) directed. Also the loop 24 enables the orthodontist to displace the straight end portion 13 forwardly or rearwardly relatively to the remainder of the facebow 10 by physically deflecting of the loop 24.

Figure 2:
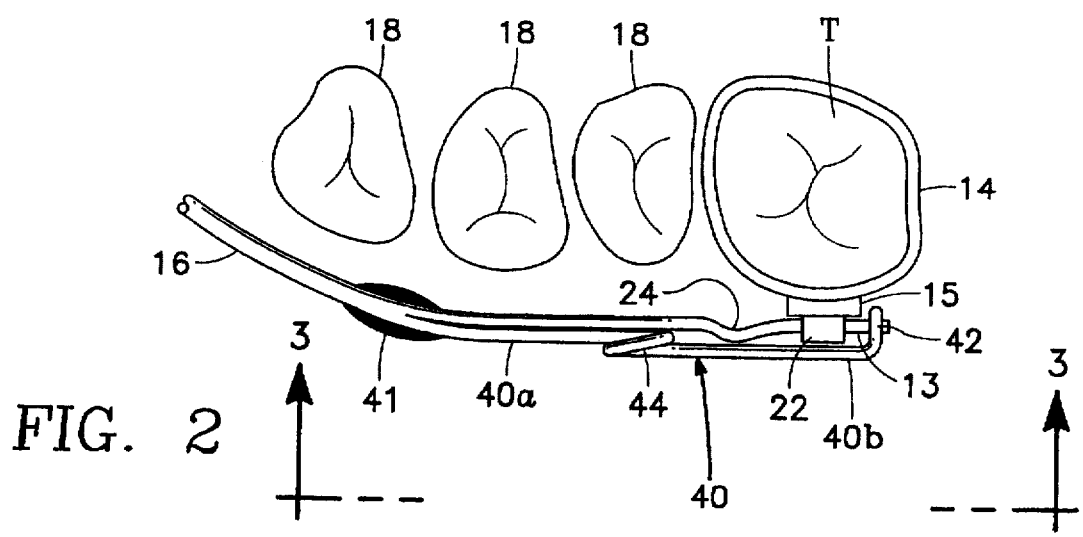
FIG. 2 is an enlarged view of the inner end of one of the arms of the inner bow of the facebow of FIG. 1.
Figure 3:
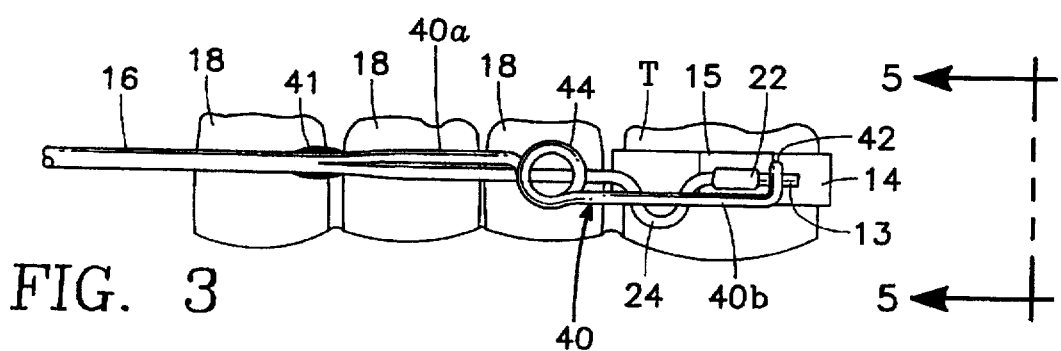
FIG. 3 is a buccal (side) view of the inner end of an arm of the inner bow taken along line 3—3 of FIG. 2.
Figure 4:
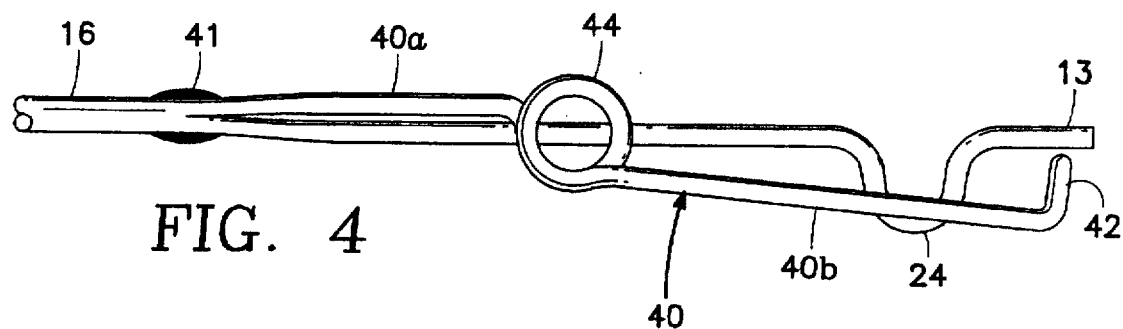
FIG. 4 is a buccal (side) view of the inner end of the same arm of the inner bow when the facebow is detached from the teeth.
Figure 5:
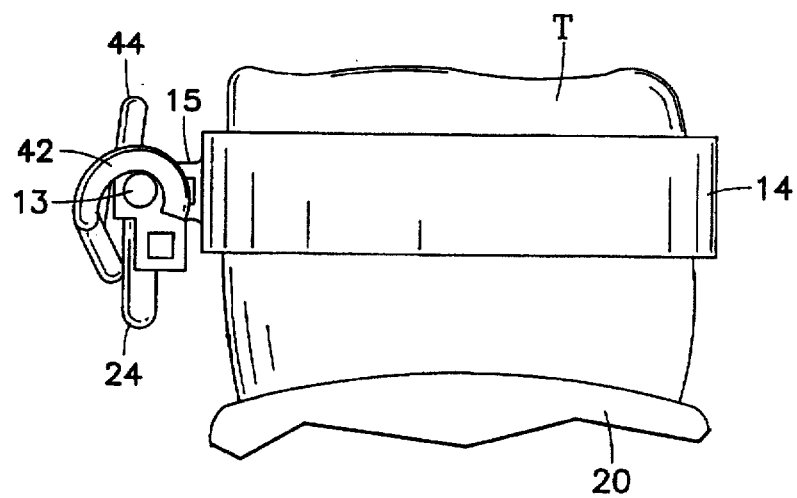
FIG. 5 is a posterior (rear) view of the inner end of an arm of the inner bow shown taken along line 5—5 of FIG. 3.

Each arm 16 and 17 of the inner bow 11 is provided with a catch 40 with there being a separate catch 40 for each arm 16 and 17. Catch 40 comprises a length of wire having one end soldered to the inner bow at mounting point 41 (of each arm 16 and 17), and then extending distally (rearwardly) to terminate, via a right angle bend, in a vertically directed hook 42 which is arranged so that it may be hooked over the straight end portion 13 of the inner bow (as is clearly shown in FIGS. 2, 3 and 5). Each catch 40 is bent into a helical loop 44 which forms a spring, biasing the hook 42 of the catch 40 occlusally (downwardly), as best seen in FIG. 4 where the hook 42 is shown not engaged with the straight end portion 13. As shown, the catch 40 comprises a first generally straight portion 40a which extends, generally parallel to the respective arm 16 or 17 of the inner bow 11, from its mounting point 41 to the helical loop 44, and then a second generally straight portion 40b which extends, again generally parallel to the respective arms 16 or 17 of the inner bow 11, from the helical loop 44 to the hook 42.

In use, the inner bow 11 of the facebow 10 is inserted into the user's mouth and each end portion 13 of its arms 16 and 17 is inserted through its respective tube 22 of the bracket 15. The user then displaces each of the locking catches 40, against the bias provided by its spring helical loop 44, to engage the hook 42 of the catch 40 over the respective end portion 13 of the inner bow 11, where it projects from the tube 22. The occlusal biasing of the catch 40, caused by the helical loop 44, ensures that the catch 40 remains engaged for as long as required. In order to remove the facebow 10, the user displaces each catch 40 slightly, against its spring bias, to disengage it from each end portion 13, after which the inner bow 11 can be withdrawn from the mouth.

Figure 6:
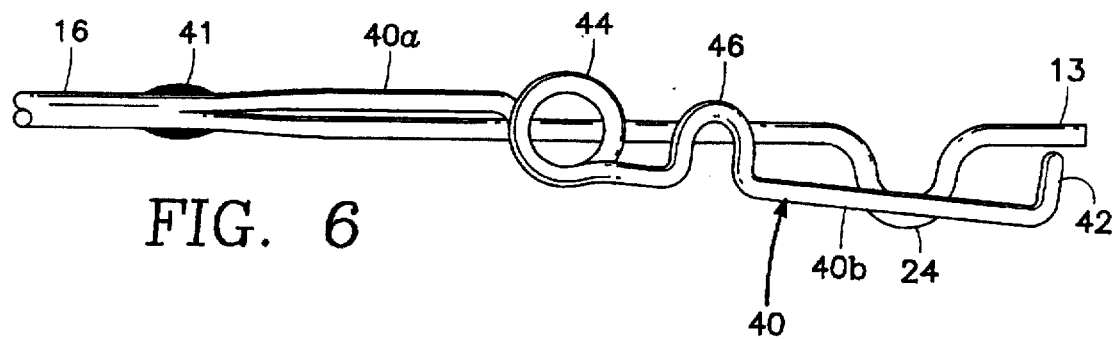
FIG. 6 is a view, similar to FIG. 4, of a modified facebow.

Referring to FIG. 6, each locking catch 40 may be formed with a loop 46 adjacent its helical loop 44, to enable the orthodontist to adjust the length of the catch 40, according to individual desires, using the loop 24, to the length of the respective arm of the inner bow 11. Adjustment of the loops 24 and 46 are to be accomplished by actually deflecting or bending of the loop 24 or 46 by means of a tool (not shown), such as a pliers, to squeeze the loop 24 or 46. The loop 46 may be gingivally directed, as shown in FIG. 6, or it may instead be occlusally directed.

Because each locking catch 40, in the above-described embodiment, engages the portion of the inner bow 11 which projects from the tube 22 of the bracket 15, the facebow 10 may be used with the brackets of various different manufacturers: in particular the length of the tubes 22 of these brackets tend to vary considerably from one manufacturer to another. Also because the catch 40 is itself relatively long, it is a simple matter for the user to engage the catch 40 with his or her finger and displace it as necessary for engaging or disengaging the catch 40 with the end portions 13 of the inner bow 11.

While the facebow 10 has been described in use with an orthodontic appliance in the form of a pair of brackets 15 fixed around an opposed pair of teeth, the facebow may be used equally well with other forms of orthodontic appliances which also include a pair of tubes which, in use, are securely positioned alongside the opposed teeth. As particular example, the facebow may be used with removable orthodontic appliances, and with functional orthodontic appliances.

In some cases, the tubes 22 may be occlusally positioned (i.e. adjacent the gum 20). The same facebow 10 may be used for the latter case, but in the opposite orientation, i.e. simply turned through 180° about its longitudinal axis: the hooked end 42 of each catch 40 then engages over the end portion 13 of the inner bow in the gingival direction, rather than in the occlusal direction.

The loop 24 may also function as a stop in conjunction with the tube 22. The loop 24 will prevent further distal movement of arm 16 and 17 relative to the respective tubes 22. Without this stop feature there would not be any force transfer between the arms 16 and 17 and the tooth mounted orthodontic appliances comprising bands 14. If the particular orthodontist does not desire to use the loop 24 as a stop, the orthodontist may install a completely separate bend in the wire between the loop 24 and the tube 22 or may install a protuberance on the wire directly adjacent to tube 22.

What is claimed is:

1. An orthodontic facebow comprising:
    an outer bow having opposite ends adapted for attachment to a strap designed to be mounted about the head and/or neck of the human, said outer bow having a first center section;
    an inner bow having a second center section, said second center section being fixedly secured to said first center section, said inner bow having a first free end and a second free end, said first free end forming a first arm adapted for connection with a first tooth mounted orthodontic appliance, said second free end forming a second arm adapted for connection with a second tooth mounted orthodontic appliance; and
    said first free end also including a first locking catch, said second free end also including a second locking catch, said first locking catch comprising an elongated first member terminating in a first hook, said second locking catch comprising an elongated second member terminating in a second hook, said first hook engaging with said first arm directly adjacent the first tooth mounted orthodontic appliance, said second engaging with said second arm directly adjacent the second tooth mounted orthodontic appliance, whereby said first and second locking catches lock said first and second arms to the first and second orthodontic appliances preventing accidental disengagement of said first and second arms from the first and second orthodontic appliances.

2. The orthodontic facebow as defined in claim 1 wherein:

said first arm having a first end portion extending distally from the first orthodontic appliance, said second arm having a second end portion extending distally from the second orthodontic appliance, said first hook engaging with said first end portion, said second hook engaging with said second end portion.

3. The orthodontic facebow as defined in claim 1 wherein:

said first locking catch being located substantially parallel to the portion of said first arm located directly adjacent to the first orthodontic appliance, said second locking catch being located substantially parallel to the portion of said second arm located directly adjacent to the second orthodontic appliance.

4. The orthodontic facebow as defined in claim 1 wherein:

said first locking catch including a first spring biasing means, said second locking catch including a second spring biasing means.

5. The orthodontic facebow as defined in claim 1 wherein:

said elongated first member comprising a first length of spring wire, said elongated second member comprising a second length of spring wire.

6. The orthodontic facebow as defined in claim 1 wherein:

said first locking catch includes a first loop capable of bending to adjust the length of said first locking catch, said second locking catch including a second loop capable of bending to adjust the length of said second locking catch.

7. The orthodontic facebow as defined in claim 6 wherein:

said first arm including a third loop capable of bending to adjust the length of said first arm, said second arm including a fourth loop capable of bending to adjust the length of said second arm.

8. The orthodontic facebow as defined in claim 1 wherein:

said first arm including a loop capable of bending to adjust the length of said first arm, said second arm including a loop capable of bending to adjust the length of said second arm.

* * * * *